United States Patent
Vilsmeier et al.

(10) Patent No.: US 11,877,809 B2
(45) Date of Patent: *Jan. 23, 2024

(54) USING A CURRENT WORKFLOW STEP FOR CONTROL OF MEDICAL DATA PROCESSING

(71) Applicant: Brainlab AG, Munich (DE)

(72) Inventors: Stefan Vilsmeier, Munich (DE); Andreas Blumhofer, Neubiberg (DE); Jens Schmaler, Mering (DE); Patrick Hiepe, Munich (DE)

(73) Assignee: BRAINLAB AG, Munich (DE)

( * ) Notice: Subject to any disclaimer, the term of this patent is extended or adjusted under 35 U.S.C. 154(b) by 325 days.

This patent is subject to a terminal disclaimer.

(21) Appl. No.: 17/281,478

(22) PCT Filed: Dec. 18, 2019

(86) PCT No.: PCT/EP2019/086073
§ 371 (c)(1),
(2) Date: Mar. 30, 2021

(87) PCT Pub. No.: WO2021/121586
PCT Pub. Date: Jun. 24, 2021

(65) Prior Publication Data
US 2022/0110693 A1 Apr. 14, 2022

(51) Int. Cl.
*A61B 5/00* (2006.01)
*A61B 34/20* (2016.01)
(Continued)

(52) U.S. Cl.
CPC .............. *A61B 34/20* (2016.02); *A61B 34/10* (2016.02); *G06T 7/0012* (2013.01); *G06V 10/17* (2022.01);
(Continued)

(58) Field of Classification Search
CPC ... A61B 34/20; A61B 34/10; A61B 2034/102; A61B 2034/105; A61B 2034/2063; A61B 2034/2065; G16H 50/50
See application file for complete search history.

(56) References Cited

U.S. PATENT DOCUMENTS

2007/0280508 A1* 12/2007 Ernst ................ G01R 33/56509
382/107
2016/0005169 A1 1/2016 Sela et al.
(Continued)

OTHER PUBLICATIONS

International Search Report and Written Opinion issued for Application No. PCT/EP2019/086073 dated Sep. 18, 2020.

*Primary Examiner* — Joel F Brutus
(74) *Attorney, Agent, or Firm* — Gray Ice Higdon (57) ABSTRACT

Disclosed is a computer-implemented of adapting a biomechanical model of an anatomical body part of a patient to a current status of the patient. The method encompasses determination of a currently executed step of a workflow such as a medical intervention, the result of the determination serving as a basis for adapting and/or updating a biomechanical model of an anatomical body part to the corresponding current status of the patient. The determination of the current workflow step may also be used as basis for controlling an imaging device for tracking entities around the patient or for imaging the anatomical body part or acquiring further data or for urging the user to perform a specific action such as acquisition of information using a tracked instrument such as a pointer. The biomechanical model has been generated from atlas data. The data sets which are generated according to the current workflow step may additionally or alternatively serve as a basis for determining the current workflow step and/or adapting the further workflow.

11 Claims, 3 Drawing Sheets

(51) Int. Cl.
    *A61B 34/10*     (2016.01)
    *G16H 50/50*     (2018.01)
    *G16H 30/40*     (2018.01)
    *G06V 10/25*     (2022.01)
    *G06V 10/10*     (2022.01)
    *G06T 7/00*     (2017.01)

(52) U.S. Cl.
    CPC ............. *G06V 10/25* (2022.01); *G16H 30/40* (2018.01); *G16H 50/50* (2018.01); *A61B 2034/102* (2016.02); *A61B 2034/105* (2016.02); *A61B 2034/2063* (2016.02); *A61B 2034/2065* (2016.02)

(56) References Cited

U.S. PATENT DOCUMENTS

2016/0236009 A1*   8/2016   Sabczynski .......... A61N 5/1037
2016/0247312 A1*   8/2016   Santhanam ............... G06T 7/33
2018/0078313 A1     3/2018   Comaniciu et al.

* cited by examiner

USING A CURRENT WORKFLOW STEP FOR CONTROL OF MEDICAL DATA PROCESSING

FIELD OF THE INVENTION

The present invention relates to a computer-implemented method of adapting a biomechanical model of an anatomical body part of a patient to a current status of the patient, a corresponding computer program, a computer-readable storage medium storing such a program and a computer executing the program, as well as a medical system comprising an electronic data storage device and the aforementioned computer.

TECHNICAL BACKGROUND

Biomechanical models are used for example to portray changes of anatomy which might be caused by a medical intervention and to accordingly update patient image data which was used for planning and navigation of the intervention. It is also known to conduct such an update on the basis of spatial sampling data like medical image data generated during the intervention.

The present invention has the object of improving use of a digital biomechanical model of an anatomical body part.

The present invention can be used for procedures e.g. in connection with medical navigation systems and image co-registration software like Cranial Navigation and Image Fusion, respectively, which are both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses determination of a currently executed step of a workflow such as a medical intervention, the result of the determination serving as a basis for adapting and/or updating a biomechanical model of an anatomical body part to the corresponding current status of the patient. The determination of the current workflow step may also be used as basis for controlling an imaging device for tracking entities around the patient or for imaging the anatomical body part or acquiring further data or for urging the user to perform a specific action such as acquisition of information using a tracked instrument such as a pointer. The biomechanical model has been generated from atlas data. The data sets which are generated according to the current workflow step may additionally or alternatively serve as a basis for determining the current workflow step and/or adapting the further workflow.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of adapting a biomechanical model of an anatomical body part of a patient to a current status of the patient. The method comprises executing, on at least one processor of at least one computer (for example at least one computer being part of a navigation system), the following exemplary steps which are executed by the at least one processor.

In a (for example first) exemplary step, initial biomechanical model data is acquired which describes an initial biomechanical model of the anatomical body part. For example, the biomechanical model is a finite element model or a coupled spring model of the anatomical body part. For example, the adapted biomechanical model data is determined by changing the boundary conditions of the finite element model or coupled spring model, respectively, for example by moving nodes, changing or adding or removing mass points, or changing or adding or removing forces. For example, the initial biomechanical model data has been generated based on an atlas-based segmentation of patient image data describing a digital medical image of the anatomical body part, i.e. by establishing a mapping between atlas data describing an image-based model of the anatomical body part and patient image data describing a digital medical image of the anatomical body part for segmenting the image representation of the anatomical body part. For example, the anatomical body part comprises at least a part of the brain or at least a part of the liver.

In a (for example second) exemplary step, workflow step data is acquired which describes a current step of a workflow of a procedure to be carried out on the patient. For example, tracking data is acquired which describes a position of a medical entity, namely at least one of a patient, medical personnel or an instrument, and workflow step definition data is acquired which describes an association between at least one position of a medical entity, namely at least one of a patient, medical personnel or an instrument, and at least one step of the workflow of the procedure to be carried out on the patient: For example, the workflow step data is then acquired based on the tracking data and the workflow step definition by comparing the position described by the tracking data to the workflow step definition data and by selecting the at least one step of the workflow being associated with a position of the medical entity corresponding to the position of the medical entity described by the tracking data as the current step of the workflow. For example, the tracking data is generated by imaging, for example video imaging, of at least one medical entity, for example at least one of the patient, the anatomical body part, medical personnel or a medical instrument. According to another example, the tracking data is generated by optically or electromagnetically tracking at least one marker device attached to at least one medical entity, for example at least one of the patient, the anatomical body part, medical personnel or a medical instrument.

In a (for example third) exemplary step, status change data is determined based on the workflow step data and the initial biomechanical model data, wherein the status change data describes a change in the patient's status. For example, the change in the patient's status is a change in at least one of a position or the geometry of the patient' body, for example of the anatomical body part, or a relative position between a medical instrument and the patient's body or a relative position between medical personnel and the patient's body, a time between changes of at least one of the aforementioned positions, a configuration or use of a medical instrument, a time interval during which a medical instrument attains a specific position or a time interval which has expired starting from a predetermined point in time during the procedure.

In a (for example fourth) exemplary step, model adaptation data is acquired which describes an association between the change in the patient's status and an adaptation to be applied to the initial biomechanical model. The adaptation is defined as for example a change in the boundary conditions of the finite element model or coupled spring model, respectively, for example by moving nodes, changing or adding or removing mass points, or changing or adding or removing forces.

In (for example fifth) exemplary step, adapted biomechanical model data is determined based on the initial biomechanical model data and the status change data and the model adaptation data, wherein the adapted biomechanical model data describes an adapted biomechanical model which is determined by applying the adaptation to the initial biomechanical model.

In an example of the method according to the first aspect, region-of-interest data is acquired based on the status change data, wherein the region-of-interest describes a region or trajectory, for example an anatomical region or an object surface, in or on which a procedure, for example the aforementioned procedure, is to be carried out. For example, the procedure comprises acquiring, based on the region-of-interest-data, instrument tracking data which describes the position of a navigated instrument. Alternatively or additionally, the procedure comprises acquiring, based on the region-of interest data, video or medical image data describing at least a part of the patient, for example the anatomical body part. For example, the procedure comprises acquiring the medical image data and the imaging device for example an ultrasound imaging probe, used for generating the medical image data is handheld or hand-guided or automatically guided, for example by a robotic arm.

In an example of the method according to the first aspect, imaging control data is determined based on the status change data. The imaging control data describes a command to be issued to a medical imaging device for taking an image of at least part of the anatomical body part. For example, the part of the anatomical body part to be imaged depends on the type of change of the patient's status. For example, the part of the anatomical body part to be imaged corresponds anatomically to the part of the biomechanical model which is adapted for determining the adapted biomechanical model data. For example, the imaging control data is transmitted to the medical imaging device and executed, so that medical image data is determined which describes a medical image of the part of the anatomical body part to be imaged.

In a second aspect, the invention is directed to a computer program comprising instructions which, when the program is executed by at least one computer, causes the at least one computer to carry out method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program, i.e. comprising the program.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:
a) the at least one computer according to the fourth aspect;
b) at least one electronic data storage device storing at least the initial biomechanical model data and the model adaptation data; and
c) a medical device for carrying out a medical procedure on the patient.

The at least one computer is operably coupled to the at least one electronic data storage device for acquiring, from the at least one data storage device, at least the initial biomechanical model data and the model adaptation data, and for storing, in the at least one data storage device, the adapted biomechanical model data.

In a sixth aspect, the invention is directed to the use of the system according to the preceding claim for conducting a medical procedure, wherein the use comprises execution of the steps of the method according to any one of the preceding method claims for adapting a biomechanical model of an anatomical body part of a patient to a current status of the patient.

For example, the invention does not involve or in particular comprise or encompass an invasive step which would represent a substantial physical interference with the body requiring professional medical expertise to be carried out and entailing a substantial health risk even when carried out with the required professional care and expertise.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein. The signal wave is in one example a data carrier signal carrying the aforementioned computer program. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT). The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
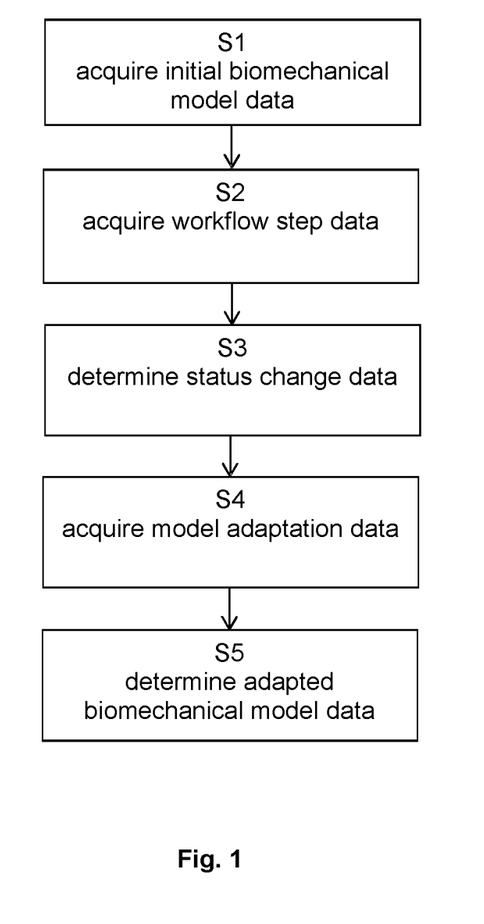
FIG. 1 illustrates a basic flow of the method according to the first aspect.

FIG. 1 illustrates the basic steps of the method according to the first aspect, in which step S1 encompasses acquisition of the initial biomechanical model data, step S2 encompasses acquisition of the workflow step data and subsequent step S3 encompasses determination of the status change data. The method then continues with acquiring the model adaptation data in step S4 and determining the adapted biomechanical model data in step S5.

Figure 2:
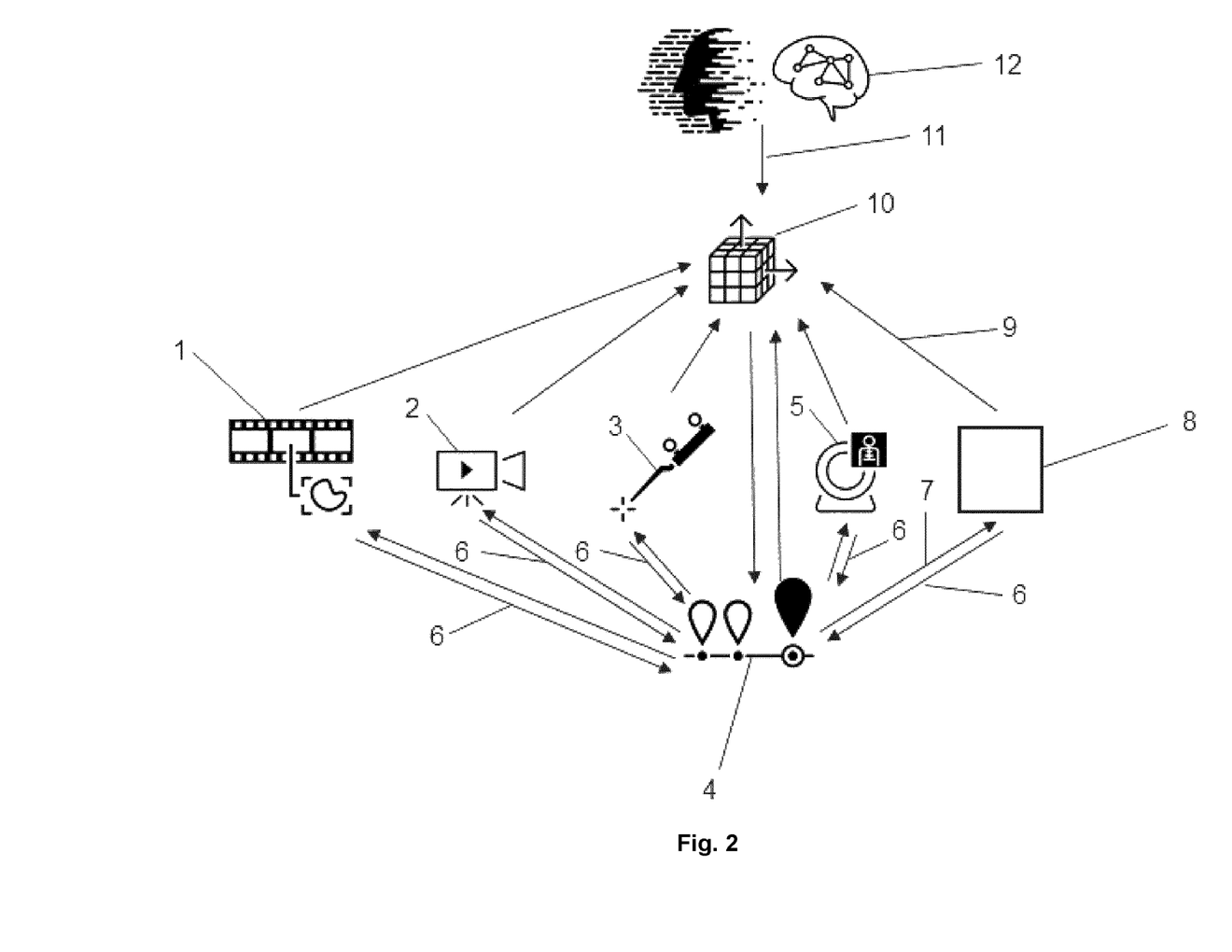
FIG. 2 shows an application of the method according to the first aspect.

FIG. 2 describes an application of the method according to the first aspect. Workflow data 4 is acquired and a current workflow data is determined so as to correspondingly adapt the biomechanical model 10. The workflow data 4 may also be used as a basis for triggering 7 the input of other intraprocedural data 8 or for using 9 the other intraprocedural data 8 for adapting the biomechanical model 10 which has initially been generated by generating 11 a model from atlas data 12. The adapted biomechanical model 10 may also be used for feedback into the workflow so as to determine the current workflow step from the adapted biomechanical model 10 e.g. if the workflow step data is replaced by up-to-date image data as basis for adapting the biomechanical model 10. The current workflow step may be determined 6 from image data taken as video data 1 or with a tracked imaging device 2 such as a microscope or from intraprocedural data 8. The image data may also be used to directly adapt the biomechanical model 10. The current workflow step may also be used to initiate imaging e.g. with a tomograph 5, wherein the generated image may be used as a basis for adapting the biomechanical model 10. Also, the current workflow step may be used as a basis for initiating acquisition of positional data with a tracked instrument 3. The image data generated with the tomograph 5 may also be used to determine the current workflow step. The current workflow step may also be used to initiate operation of a video camera for generating the image data 1 or the tracked imaging device 2. Use of the tracked pointer 3 may also be used as a basis for determining the current workflow step.

Figure 3:
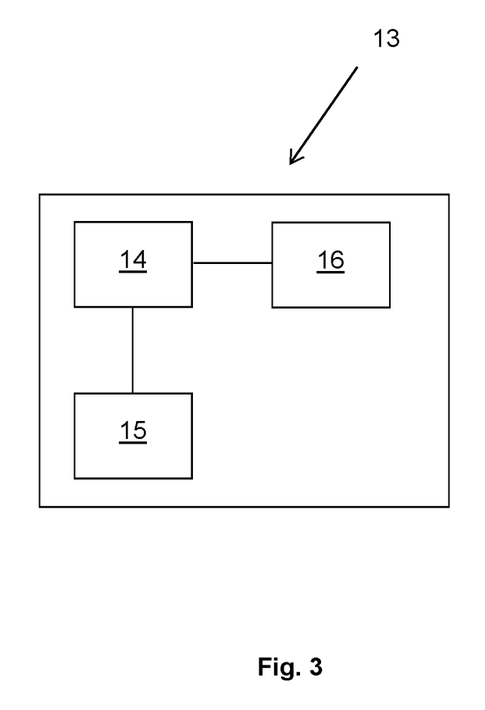
FIG. 3 is a schematic illustration of the system according to the fifth aspect.

FIG. 3 is a schematic illustration of the medical system 13 according to the fifth aspect. The system is in its entirety identified by reference sign 13 and comprises a computer 14, and an electronic data storage device (such as a hard disc) 15 for storing at least the patient data. The components of the medical system 13 have the functionalities and properties explained above with regard to the fifth aspect of this disclosure.

The following exemplary aspects are also part of possible embodiments of the invention.

The initial biomechanical model data is generated based on physical, e.g. mechanical, properties of the tissue types, e.g. tissue classes, stored in the atlas.

The workflow step data can be generated based on intraoperative image data, e.g. from an x-ray device, fluoroscopy device, x-ray tomograph, magnetic resonance tomograph, C-arm, on intraoperative video data, e.g. from an endoscope or microscope or exoscope or external camera with a field of view to the surgical site, on ultrasound image data, on the position, speed and acceleration of instruments or imaging devices, e.g. as a function of time. The workflow step data can be based on contents of the intraoperative video data, such as a position or speed or acceleration of an instrument or implant or an anatomical object in an image, e.g. as a function of time.

The workflow step data can also be based on other intraoperative or intraprocedural data, such as the status of a device in the operating room, e.g. "switched on" or "switched off", the device can be for example an anaesthesia device. Physiological data of the patient.

The workflow step data can be determined by comparing the intraoperative data to predetermined criteria, such as a predetermined pattern for the other intraoperative image data, video data or other intraoperative data using a predetermined relation between the pattern and a workflow step.

The workflow step data can also be determined using a learning algorithm: In a learning phase, the events are labelled manually and input into a learning algorithm together with the intraoperative data. The learning algorithm is e.g. based on a Convolutional Neural Network or Recurrent Neural Network. During the using phase of the learning algorithm, which takes place after the learning phase, the intraoperative data are input and the event is output by the learning algorithm based on the learning data acquired during the learning phase.

The workflow step data can also be based on a stored workflow for the type of procedure performed. Such a stored workflow consists of a number of predetermined steps.

The current step of the workflow is e.g. opening of the dura, the performing of a resection, performing a craniotomy, installation of a drainage, setup of the patient, use of a suction device, suction of cerebrospinal fluid, tissue removal, application of pharmaceuticals.

The status change data comprises e.g. that the dura was opened, that a resection was performed, that instruments are in place.

A handheld or hand-guided or automatically guided imaging device is e.g. an ultrasound probe, a microscope or an endoscope.

To support image acquisition with a handheld device, the ROI can be indicated to a user on a display, e.g. an augmented reality display.

The invention claimed is:

1. A computer-implemented method of adapting a biomechanical model of an anatomical body part of a patient to a current status of the patient, the method comprising:
acquiring initial biomechanical model data which describes an initial biomechanical model of the anatomical body part;
acquiring workflow step data which describes a current step of a workflow of a procedure to be carried out on the patient;
determining status change data based on the workflow step data and the initial biomechanical model data, wherein the status change data describes a change in the patient's status, the change in the patient's status being a change in at least one of a position or a geometry of the patient's body;
acquiring model adaptation data which describes an association between the change in the patient's status and an adaptation to be applied to the initial biomechanical model;
determining adapted biomechanical model data based on the initial biomechanical model data and the status change data and the model adaptation data, wherein the adapted biomechanical model data describes an adapted biomechanical model which is determined by applying the adaptation to the initial biomechanical model; and
the method further including
determining imaging control data based on the status change data, wherein the imaging control data describes a command to be issued to a medical imaging device for taking an image of at least part of the anatomical body part.

2. The method according to claim 1, comprising a step in which
acquiring region-of-interest data based on the status change data, wherein the region-of-interest describes a region, in which a procedure is to be carried out.

3. The method according to claim 2, wherein the procedure comprises
acquiring, based on the region-of-interest data, instrument position data which describes the position of a navigated instrument or acquiring, based on the region-of-interest data, medical image data describing at least a part of the patient anatomical body part.

4. The method according to claim 1, wherein the part of the anatomical body part to be imaged depends on the type of change of the patient's status.

5. The method according to claim 4, wherein the part of the anatomical body part to be imaged corresponds anatomically to a part of the biomechanical model which is adapted for determining the adapted biomechanical model data.

6. The method according to claim 5, wherein the imaging control data is transmitted to the medical imaging device and executed, so that medical image data is determined which describes the medical image of the part of the anatomical body part to be imaged.

7. The method according to claim 1, wherein the biomechanical model is a finite element model or a coupled spring model of the anatomical body part, and wherein the adapted biomechanical model data is determined by changing boundary conditions of the finite element model or the coupled spring model, respectively, by moving nodes, changing or adding or removing mass points, or changing or adding or removing forces.

8. The method according to claim 1, wherein the initial biomechanical model data has been generated based on an atlas-based segmentation of patient image data describing a digital medical image of the anatomical body part.

9. The method according to claim 1, further comprising:
acquiring tracking data which describes a position of a medical entity, namely at least one of a patient, medical personnel or an instrument;
acquiring workflow step definition data which describes an association between at least one position of a medical entity, namely at least one of a patient, medical personnel or an instrument, and at least one step of the workflow of the procedure to be carried out on the patient; and
acquiring the workflow step definition data based on the tracking data and the workflow step definition data by comparing the position described by the tracking data to the workflow step definition data and by selecting the at least one step of the workflow being associated with a position of the medical entity corresponding to the position of the medical entity described by the tracking data as the current step of the workflow.

10. A non-transitory computer-readable program storage medium comprising instructions which, when executed by at least one processor on at least one computer, cause the at least one computer to:
acquire initial biomechanical model data which describes an initial biomechanical model of an anatomical body part;
acquire workflow step data which describes a current step of a workflow of a procedure to be carried out on a patient;
determine status change data based on the workflow step data and the initial biomechanical model data, wherein the status change data describes a change in the patient's status, the change in the patient's status being a change in at least one of a position or a geometry of the patient's body;
acquire model adaptation data which describes an association between the change in the patient's status and an adaptation to be applied to the initial biomechanical model;
determine adapted biomechanical model data based on the initial biomechanical model data and the status change data and the model adaptation data, wherein the adapted biomechanical model data describes an adapted biomechanical model which is determined by applying the adaptation to the initial biomechanical model; and
the method further including
determining imaging control data based on the status change data, wherein the imaging control data describes a command to be issued to a medical imaging device for taking an image of at least part of the anatomical body part.

11. A medical system, comprising:
at least one computer having instructions stored on associated memory, the instructions when executed on at least one processor of the at least computer operable to:
acquire initial biomechanical model data which describes an initial biomechanical model of an anatomical body part;
acquire workflow step data which describes a current step of a workflow of a procedure to be carried out on a patient;
determine status change data based on the workflow step data and the initial biomechanical model data, wherein the status change data describes a change in the patient's status, the change in the patient's status being a change in at least one of a position or a geometry of the patient's body;
acquire model adaptation data which describes an association between the change in the patient's status and an adaptation to be applied to the initial biomechanical model;
determine adapted biomechanical model data based on the initial biomechanical model data and the status change data and the model adaptation data, wherein the adapted biomechanical model data describes an adapted biomechanical model which is determined by applying the adaptation to the initial biomechanical model;
determine imaging control data based on the status change data,
wherein the imaging control data describes a command to be issued to a medical imaging device for taking an image of at least part of the anatomical body part;
at least one electronic data storage device storing at least the initial biomechanical model data and the model adaptation data; and
a medical device for carrying out a medical procedure on the patient,
wherein the at least one computer is operably coupled to the at least one electronic data storage device for acquiring, from the at least one electronic data storage device, at least the initial biomechanical model data and the model adaptation data, and for storing, in the at least one electronic data storage device, the adapted biomechanical model data.

* * * * *